United States Patent
Liu et al.

(10) Patent No.: US 9,884,894 B2
(45) Date of Patent: Feb. 6, 2018

(54) FINE EPITOPE PEPTIDE CAPABLE OF INDUCING CROSS-REACTIVE ANTIBODIES AMONG HOMOLOGOUS PROTEINS IN HUMAN PAPILLOMA VIRUS E6 PROTEIN

(71) Applicants: Guangzhou Hengsun Pharmaceutical Technology Co. Ltd., Guangzhou (CN); Riting Liu, Guangzhou (CN)

(72) Inventors: Riting Liu, Guangzhou (CN); Wanxiang Xu, Shanghai (CN)

(73) Assignees: Guangdong Nanwan Pharmaceutical Technology Co. Ltd., Guangzhou (CN); Riting Liu, Guangzhou (CN)

(*) Notice: Subject to any disclaimer, the term of this patent is extended or adjusted under 35 U.S.C. 154(b) by 0 days.

(21) Appl. No.: 14/907,421

(22) PCT Filed: Aug. 5, 2013

(86) PCT No.: PCT/CN2013/080798
§ 371 (c)(1),
(2) Date: Jan. 25, 2016

(87) PCT Pub. No.: WO2015/010347
PCT Pub. Date: Jan. 29, 2015

(65) Prior Publication Data
US 2016/0168206 A1 Jun. 16, 2016

(30) Foreign Application Priority Data
Jul. 24, 2013 (CN) .......................... 2013 1 0314415

(51) Int. Cl.
| | | |
|---|---|---|
| C07K 14/025 | (2006.01) | |
| A61K 39/12 | (2006.01) | |
| C07K 14/005 | (2006.01) | |
| C07K 16/08 | (2006.01) | |
| G01N 33/569 | (2006.01) | |
| C12N 7/00 | (2006.01) | |
| A61K 39/00 | (2006.01) | |
| C12Q 1/70 | (2006.01) | |

(52) U.S. Cl.
CPC ............ *C07K 14/005* (2013.01); *A61K 39/12* (2013.01); *C07K 16/084* (2013.01); *C12N 7/00* (2013.01); *G01N 33/56983* (2013.01); *A61K 2039/585* (2013.01); *A61K 2039/64* (2013.01); *C07K 2317/33* (2013.01); *C07K 2317/34* (2013.01); *C12N 2710/20022* (2013.01); *C12N 2710/20034* (2013.01); *C12Q 1/708* (2013.01); *C12Q 2600/158* (2013.01); *G01N 2333/025* (2013.01)

(58) Field of Classification Search
None
See application file for complete search history.

(56) References Cited

U.S. PATENT DOCUMENTS 5,932,412 A  8/1999  Dillner et al.
7,288,258 B2 10/2007  Choppin et al.

FOREIGN PATENT DOCUMENTS

WO  2010-037395 A2  4/2010

OTHER PUBLICATIONS

GenBank: ACR25130.1. E6 [Human papillomavirus type 16]. Nov. 1, 2009.*
Mirshahabi et al. Production of human papilloma virus type 16 e6 oncoprotein as a recombinant protein in eukaryotic cells. Iran J Cancer Prev. 2012 Winter;5(1):16-20.*
de Villiers, Ethel-Michele, et al., "Classification of papillomaviruses"; Virology, vol. 324 (2004); Elsevier Inc., doi: 10.1016/j.virol.2004.03.033; pp. 17-27 (11 pages).
Parkin, Donald Maxwell; "The global health burden of infection-associated cancers in the year 2002"; Int. J. Cancer, vol. 118 (2006); published online Jan. 10, 2006 in Wiley InterScience (www.interscience.wiley.com; DOI: 10.1002/jc.21731); pp. 3030-3044 (15 pages).
de Sanjose, Silvia, et al., "Human papillomavirus genotype attribution in invasive cervical cancer: a retrospective aross-sectional worldwide study"; Lancet Oncology, vol. 11, Nov. 2010; published online Oct. 18, 2010, www.thelancet.com/oncology, DOI: 10.1016/S1470-2045(1)70230-8; pp. 1048-1056 (9 pages).
Wheeler, Cosette M., et al., Cross-protective efficacy of HPV-16/18 AS04-adjuvanted vaccine against cervical infection and precancer caused by non-vaccine oncogenic HPV types: 4-year end-of-study analysis of the randomised, double-blind Patricia trial; Lancet Oncology, vol. 13 (Jan. 2012); published online Nov. 9, 2011, DOI: 10.106/S1470-2045(11)70287-X; pp. 100-110 (11 pages).
Huang, et al., "Human papillomavirus types 52 and 58 are prevalent in cervical cancer from Chinese women"; Article in International Journal of Cancer (Nov. 1997);vol. 73; DOI: 10.1002/(SICI)1097-0215(19971127)73:5<775:AID-IJC27>3.0.CO;2-3; pp. 775-776 (3 pages).
Dillner, Joakim, "Mapping of Linear Epitopes of Human Papillomavirus Type 16: The El, E2, E4, E5, E6 and E7 Open Reading Frames"; Int. J. Cancer, vol. 46, Issue 4 (1990); pp. 703-711 (9 pages).
Dillner, J., et al., "Synthetic peptides in human papillomavirus 1, 5, 6, 8, 11, 16, 18, 31, 33 and 56, useful in immunoassay for diagnostic purposes"; See: U.S. Pat. No. 5,932,412 dated Aug. 3, 1999.

(Continued)

*Primary Examiner* — Nianxiang Zou
(74) *Attorney, Agent, or Firm* — Osha Liang LLP (57) ABSTRACT

This invention relates to the minimal motif of an epitope on the E6 protein from human papilloma virus (HPV), and this minimal motif of the epitope induces a monoclonal antibody having cross-reactivity with some homologous proteins of HPVs. The inventors are the first to identify a fine antigenic epitope only existing conservatively on the E6 proteins of high risk HPV16, 33, 52 or 58). Therefore, the peptides comprising this epitope can be used to prepare immunogen or serological detection antigen against the HPV E6 proteins, or to prepare specific universal antibodies for a variety of high-risk/carcinogenic HPVs.

5 Claims, 3 Drawing Sheets

(56) References Cited

OTHER PUBLICATIONS

Ku, Wan-Xiang, et al., "Minimal motif mapping of a known epitope on human zona pellucida protein-4 using a peptide biosynthesis strategy"; Journal of Reproductive Immunology, vol. 81 (2009); Elsevier, doi: 10.1016/j.jri.2009.04.004; pp. 9-16 (8 pages).

Bleul, Conrad, et al., "Human Papillomavirus Type 18 E6 and E7 Antibodies in Human Sera: Increased Anti-E7 Prevalence in Cervical Cancer Patients"; Journal of Clinical Microbiology, Aug. 1991; American Society for Microbiology (1991), 0095-1137/91/081579-105$02.00/0; pp. 1579-1588 (10 pages).

Banks, Lawrence, et al., "Identification of Human Papillomavirus Type 18 E6 Polypeptide in Cells Derived from Human Cervical Carcinomas"; J. Gen. Virol. (1987), vol. 68; pp. 1351-1359 (9 pages).

Kohler, G., et al., "Derivation of specific antibody-producing tissue culture and tumor lines by cell fusion"; Eur. J. Immunol., vol. 6 (1976); pp. 511-519 (9 pages).

Kohler, G., et al., "Fusion between immunoglobulin-secreting and nonsecreting myeloma cell lines"; Eur. J. Immunol., vol. 6 (1976); pp. 292-295 (4 pages).

Gao, L., et al., "Immune response to human papillomavirus type 16 E6 gene in a live vaccinia vector"; Journal of General Virology, vol. 75 (1994); pp. 157-164 (8 pages).

International Search Report and Written Opinion dated May 19, 2014, issued by the State Intellectual Property Office (SIPO) of the Peoples Republic of China in related International Application No. PCT/CN2013/080798, with English translation (10 pages).

PCT International Preliminary Report on Patentability and Written Opinion (IPRP) dated Jan. 26, 2016, issued by the International Bureau of WIPO in related International Application No. PCT/CN2013/080798, with English translation (10 pages).

\* cited by examiner

| HPV subtype | E6 Protein Size (Amino Acid) | Conservative Sequence | SEQ ID NOs | Similarity Rate | Risk Classification |
| --- | --- | --- | --- | --- | --- |
| 58 | 149 | SLYGDTLE | SEQ ID NO: 9 | - | high-risk |
| 16 | 158 | SLYGTTLE | SEQ ID NO: 16 | 80% | most high-risk |
| 18 | 158 | SVYGDTLE | SEQ ID NO: 17 | 100% | most high-risk |
| 31 | 149 | SVYGTTLE | SEQ ID NO: 18 | 80% | high-risk |
| 33 | 149 | SVYGHTLE | SEQ ID NO: 19 | 80% | high-risk |
| 35 | 149 | SVYGETLE | SEQ ID NO: 20 | 80% | high-risk |
| 45 | 158 | SVYGETLE | SEQ ID NO: 20 | 80% | high-risk |
| 52 | 148 | SLYGKTLE | SEQ ID NO: 21 | 80% | high-risk |
| 56 | 155 | SVYGATLE | SEQ ID NO: 22 | 80% | high-risk |
| 66 | 155 | SVYGATLE | SEQ ID NO: 22 | 80% | high-risk |
| 69 | 151 | SVYGATLE | SEQ ID NO: 22 | 80% | high-risk |
| 82 | 151 | SVYGATLE | SEQ ID NO: 22 | 80% | high-risk |

Figure 1

| HPV Subtype | E6 Protein Size (Amino Acid) | Similar Sequence Comparison | SEQ ID NOs |
|---|---|---|---|
| 58 | 149 | IS$^{75}$EYRHY$^{79}$NY | SEQ ID NO: 23 |
| 18 | 158 | IS$^{77}$ELRHY$^{81}$SD | SEQ ID NO: 24 |
| 16 | 158 | IR$^{82}$EYRHY$^{86}$CY | SEQ ID NO: 25 |
| 33 | 149 | IS$^{75}$EYRHY$^{79}$NY | SEQ ID NO: 26 |
| 52 | 148 | IS$^{75}$EYRHY$^{79}$QY | SEQ ID NO: 27 |

SEQUENCE LISTING

```
<160> NUMBER OF SEQ ID NOS: 8

<210> SEQ ID NO 1
<211> LENGTH: 5
<212> TYPE: PRT
<213> ORGANISM: Human papillomavirus

<400> SEQUENCE: 1

Glu Leu Arg His Tyr
1               5

<210> SEQ ID NO 2
<211> LENGTH: 5
<212> TYPE: PRT
<213> ORGANISM: Human papillomavirus

<400> SEQUENCE: 2

Glu Tyr Arg His Tyr
1               5

<210> SEQ ID NO 3
<211> LENGTH: 22
<212> TYPE: PRT
<213> ORGANISM: Human papillomavirus

<400> SEQUENCE: 3

Ile Asp Phe Tyr Ser Arg Ile Arg Glu Leu Arg His Tyr Ser Asp Ser
1               5                   10                  15

Val Tyr Gly Asp Thr Leu
            20

<210> SEQ ID NO 4
<211> LENGTH: 8
<212> TYPE: PRT
<213> ORGANISM: Human papillomavirus

<400> SEQUENCE: 4

Ser Leu Tyr Gly Asp Thr Leu Glu
1               5

<210> SEQ ID NO 5
<211> LENGTH: 15
<212> TYPE: PRT
<213> ORGANISM: Human papillomavirus

<400> SEQUENCE: 5

Leu Arg Leu Leu Ser Lys Ile Ser Glu Tyr Arg His Tyr Asn Tyr
1               5                   10                  15

<210> SEQ ID NO 6
<211> LENGTH: 15
<212> TYPE: PRT
<213> ORGANISM: Human papillomavirus

<400> SEQUENCE: 6
```

```
Ile Ser Glu Tyr Arg His Tyr Asn Tyr Ser Leu Tyr Gly Asp Thr
1               5                   10                  15

<210> SEQ ID NO 7
<211> LENGTH: 9
<212> TYPE: PRT
<213> ORGANISM: Human papillomavirus

<400> SEQUENCE: 7

Ile Ser Glu Tyr Arg His Tyr Asn Tyr
1               5

<210> SEQ ID NO 8
<211> LENGTH: 8
<212> TYPE: PRT
<213> ORGANISM: artificial sequence
<220> FEATURE:
<223> OTHER INFORMATION: peptide

<400> SEQUENCE: 8

Ala Ala Ala Glu Tyr Arg His Tyr
1               5
```

FINE EPITOPE PEPTIDE CAPABLE OF INDUCING CROSS-REACTIVE ANTIBODIES AMONG HOMOLOGOUS PROTEINS IN HUMAN PAPILLOMA VIRUS E6 PROTEIN

CROSS REFERENCE TO RELATED APPLICATIONS

This is a national stage application of PCT/CN2013/0080798, filed on Aug. 5, 2013, which claims the priority of Chinese Patent Application No. CN-201310314415.1, filed on Jul. 24, 2013. This application claims the benefit and priority of these prior applications and incorporates their disclosures by reference in their entirety.

FIELD OF THE INVENTION

This invention relates to the field of immunology and bio-medical technology. Specifically, it relates to the minimal motif of a linear B-cell epitope on the E6 protein from human papillomaviruses (HPVs) as well as its applications. This epitope motif can be recognized by the monoclonal antibody (mAb) C1P5.

BACKGROUND OF THE INVENTION

Cervical cancer is currently the second most lethal cancer threatening women globally after breast cancer. Each year about 500,000 people are diagnosed as cervical cancer in the world, and about 300,000 people died of this cancer. In China the incidence rate of cervical cancer each year is estimated to be around 135,000 people, and around 50,000 people died of this cancer. It was confirmed in early 1980's that cervical cancer is correlated with human papillomavirus (HPV) infection. Recent data demonstrated that 99.8% of the biopsy samples of cervical cancer were detected to be infected with HPV. Therefore, in care of the reproductive health of women, scientific researchers of various countries have been conducted research on the diagnosis, prevention, and treatment of HPV. It is exciting that the first tetravalent and bivalent HPV prophylactic vaccines (Gardasil and Cervarix) were successfully developed respectively by Merck in the U.S. in 2006 and by GlaxoSmithKline (GSK) in UK in 2007.

However, in terms of HPV prevention and treatment, currently there remain many issues that need to be addressed. It is now clear, for example, that there are 120 of HPV subtypes that can infect the epithelial tissue of female genital tracts, of which approximately 40 are high-risk HPVs (HR-HPVs) resulting in cervical cancer (1-3). The prophylactic HPV vaccines, Gardasil and Cervarix mentioned above, that have been approved for clinical usage in many countries, are mainly aimed only at the most prevalent HPV 16 and 18subtypes, although they also showed a certain degree of protection against other HR-HPVs (4). Therefore, development of "universal" HPV vaccines becomes a widely concerned topic undoubtedly, and they are particularly important to the women in China or Asian, since the HPV58 and HPV52 subtypes are more prevalent than HPV18 after HPV16 among the HR-HPVs that infect women in this region, while HPV18 is usually ranked second after HPV16 in many areas (5).

In addition, both HPV tetravalent vaccine made by Merck and the bivalent vaccine by GlaxoSmithKline have very complicated production processes and very high comprehensive costs, and the prices of these vaccines are obviously not suitable for their promotion and application in developing countries. Thus it is currently an important approach or direction to develop recombinant multiple-epitope peptide vaccines that could be more easily manufactured and stored, and could possess lower prices. Although current HPV therapeutic peptide vaccines mainly select cytotoxic T cell epitope (TCL/TcCE) of the E6 and E7 proteins against HPV 16 and 18 as immunogen, there were reports about the development of therapeutic HPV vaccines of fusion protein that simultaneously induced $CD4^+$, $CD8^+$-mediated and antibody-mediated immune responses by targeting at early carcinogenic E6 and E7 proteins, implicating the possibility of developing prophylactic HPV vaccines of multiple-epitope peptides that combine B- and T-cell epitopes, i.e., achieving the effects of completely or partially removal of HPV by both the humoral response of antibody production and the tumor-specific cellular immune response before the occurrence of precancerous or cervical malignant lesions.

Moreover, in the clinical practice, it is always an important topic to develop a simple, accurate and sensitive serological detection method for HPV infection, a method lying between cytology observation and DNA diagnosis. The core content or technology of the methodology is the identification of antibodies induced by HPVs in the patient's serum as well as the linear antigen epitopes of the induced antibodies (6), followed by the synthesis of the epitope peptides that serve as detection antigen for establishing ELISA detection method. However, so far there has been no a serological detection kit that could be used in clinical diagnosis for HPV infection due to the difficulty in ruling out the high false-positive rates by using the above ELISA detection method, and such a high false-positive rates could not be accepted by both doctors and patients. It is conceivable that the false-positive results are caused by three factors: 1) low titers of antibodies in patients induced by HPV infection, resulting in low extent of dilution of the serum samples (commonly used serum dilutions: 1:2-1:10); 2) there are usually a large number of antibodies against unknown antigens in human serum due to many factors such as its resistance to microbial infections including viruses as well as autoimmunity; 3) take for example to use a single 18~20-mer epitope peptide as detection antigen (7), it is known that a linear B cell epitope usually comprises of 3 to 8 amino acid (aa) residues, suggesting obviously that there are a large number of potential epitopes composed of more than 3-8 residues on the peptide, and such epitopes can be identified by unknown antibodies. Thus there is a high probability that such a peptide can be recognized by one or several unknown antibodies in the body at lower extent of dilution of the patient's serum. On the basis of the knowledge above, it is believe that in the future in order to develop detection antigens of synthetic peptide with high specificity and sensitivity, the direction for making innovative breakthrough should be: 1) it would be better to make detection antigen comprising the minimal motif of epitope or its extended 8-mer peptide, so that its cross reactions with unknown antibodies would be minimized, thus improving its detection specificity; 2) to make detection antigen peptide comprising the minimal motifs of multiple epitopes as to identify antibodies against multiple epitopes of the target protein. This approach can increase the extent of dilution of the serum samples by enriching the antibodies of lower titer and via the amplifying effect of coupling the second antibody, resulting in the improved detection sensitivity for the target antibodies. However, the non-target antibodies at the same low titer will fall below the detection sensitivity as the extent of dilution of the serum sample increases, thus reducing the potential cross reactivity with the detection antigen and thus avoiding false positive results. Obviously, the success of developing the detection antigen kit described above would rely on the successful identification of more of the linear epitopes of the target antigen as well as their minimal motifs.

In view of the actual needs of developing HPV vaccines and diagnostic reagents, we have previously completed the identification of all four linear epitopes and their minimal motifs of the HPV58-E6 protein (8). We found that the sequence of 84YGDTL88 on the E6-2 epitope of HPV58 is highly conservative among the homologous proteins of the high-risk HPVs (FIG. 1), and this sequence is the same as the five residue sequence at the C-terminal of the HPV18-E6/2 antigenic peptide with 22 aa residues (9).

As is known to all, one antigen epitope produces one kind of antibody, and one antibody corresponds to one epitope. In view of the potential applications of epitopes and antibodies in developing antiviral or antitumor drugs (vaccines) as well as diagnostic reagents, it has no doubt that identification and preparation of epitopes are inventions creating intellectual property rights. Of course, the reason for granting intellectual property rights to such efforts in identification and preparation of epitopes relies on the difficulty of the technology used in the pursuit. Banks L et al., for example, prepared six strains of monoclonal antibodies (mAbs) including C1P5 against recombinant HPV18 E6 protein (10), but did not identify their epitopes and their antibody-recognizing minimal motifs, and thus failed to find that the mAbs C1P5 had cross-reactivity with the homologous proteins of other high-risk HPVs in addition to HPV16-E6 (thus losing other potential applications of C1P5). They also failed to identify the epitopes recognized by the other five strains of mAbs named D2A6, C1N1, C1X1, B1B3 and B1A2. It is also very important to identify the epitopes recognized by the other five mAbs. The subtypes of the five strains of monoclonal antibodies might be different. There are possibilities that the same epitope motif could be recognized by two or more strains of monoclonal antibodies of different subtypes. In another study, for example, two different strains of mAbs with different subtypes (G1 and G3) against HPV18-E6 protein could recognize likewise the four residues motif of 7PTRR10 (11). However, restricted by the methodology of epitope identification, very few researches in this aspect were reported previously. The reason is that the previous technologies of epitope identification including chemical synthetic peptide methodology are difficult to operate, even when the monoclonal antibodies were available to be used for identifying the epitopes.

Therefore, obviously it has great significance in the field to identify the minimal motifs of epitopes of the new monoclonal antibodies by employing our improved biosynthetic peptide method.

DETAILED DESCRIPTION OF THE INVENTION

This invention is to provide a kind of epitope minimal motif peptide on the E6 protein of HPV18 and its applications, which can be recognized by mAb C1P5.

The first aspect of this invention is to provide a type of separated peptides, its characteristics is described by the type of peptides comprising the sequence of amino acid residues as shown by formula (I);

EXRHY  (I);

X represents the amino acid L or Y;
and the described peptides are derived from E6 proteins of HPVs.

In a preferential example, the peptide described here possesses the amino acid sequence as shown in SEQ ID NO: 1 or SEQ ID NO: 2.

In another preferential example, the peptide described here derives from the E6 protein of HPV18 (X representing L), HPV16 (X representing Y), HPV52 (X representing Y), HPV33 (X representing Y) or HPV58 (X representing Y).

Another aspect of this invention provides the application of the previously described peptide to prepare immunogen against E6 protein of human papillomavirus.

In the preferential examples, the HPVs described here are HPV16, HPV18, HPV33, HPV52, or HPV58.

Another aspect of this invention provides the application of the previously described peptide to prepare antibodies that can specifically bind to the E6 protein of HPVs. Preferentially, the HPVs described here are HPV16, HPV18, HPV33, HPV52, or HPV58.

Another aspect of this invention provides the application of the previously described peptide to prepare detection antigen of multiple epitopes by itself or in combination with others for serological diagnosis of the HPV18 infection.

Another aspect of this invention provides the application of the previously described peptide to be used as markers or reference for diagnosing the infection of HPV16, HPV18, HPV33, HPV52, or HPV58 according to the encoded amino acid sequence of the E6 gene that could be amplified by PCR.

Another aspect of this invention provides the application of mAb C1P5 to prepare kits for detecting HPVs, and the HPVs described here are HPV33, HPV52, or HPV58.

Another aspect of this invention provides a kit for detecting HPVs, and the HPVs described here are HPV33, HPV52, or HPV58, and the kit described here includes the mAb C1P5.

Many other aspects or embodiments of this invention can be made, and they are obvious to the technical personnel in the field according to the published content of this invention.

EXPERIMENTAL METHODS

After extensive research, the inventors were the first to use commercially available mAb C1P5 to identify a unique epitope motif on HPV18-E6 protein, which is highly conserved among the several E6 homologous proteins of HR-HPVs including HPV16, HPV33, HPV52 and HPV58. Therefore, the peptide (also called short peptide or epitope minimal motif peptide in this invention) containing this epitope can be used to prepare vaccine immunogen (or to prepare immunogen of multiple-epitope peptides in combination with other epitopes), or to prepare specific antibodies targeting the E6 proteins of HR-HPV33, 52 and 58. These immunogens (vaccines) or antibodies can be used for the prevention against the five HR-HPVs or for the diagnosis of HR-HPVs infections.

DEFINITIONS

As used herein, "separated" means a status that the substance is separated from their original state (if it is a natural substance, the original state is the natural state). For example, polynucleotide or polypeptide (peptide) at the natural state with cells is not separated and purified. But the same polynucleotide or polypeptide (peptide) is separated and purified if they are separated from other existing substance of natural state.

As used herein, "E6 protein" means a protein that exists in HPV. In this invention, the coding gene sequences and the sequences of the protein primary structure of E6 proteins of HPV16, HPV18, HPV33, HPV52 and HPV58 are in accordance to their standard strains respectively, and their registration numbers at GenBank are in turn NC_001526, NC_001357, EU918766, X74481 and D90400 respectively.

As used herein, "comprising," "having," "containing," or "including" are open-ended terms that encompass "consisting essentially of," "consisting mainly of" and "consisting of." "Consisting essentially of," "consisting mainly of" and "consisting of" belong to the subordinate concept under "comprising," "having," "containing," or "including."

As use herein, "specificity" of an antibody means that the antibody is able to bind to the E6 proteins or their fragments of certain subtypes of HPVs, particularly referring to an antibody that can bind with the E6 proteins of the unique or particular HPV subtypes.

Antigen Epitope and its Applications

In the process of research, the inventors analyzed a strain of commercially available mAb C1P5 against HPV18-E6 protein to determine whether it is able to recognize HPV58E6-2 epitope, and then further identified the C1P5-binding epitope minimal motif on HPV18 E6 protein. In the process of sequence analysis and experiment, the inventors unexpectedly discovered that the mAb C1P5 could bind to the recombinant HPV58E6 protein in Western blotting, but it did not recognize the octapeptide (SLYGDTLE: SEQ ID NO: 9) fused with GST188 carrier protein, thus suggesting C1P5-recognizing site is not in this octapeptide that is 100% conserved between HPV18- and 58-E6 proteins. Then, the inventors carried out research on epitope mapping of HPV18-E6 protein by employing unique strategies, and finally came out with the technical protocol of this invention.

Figure 1:
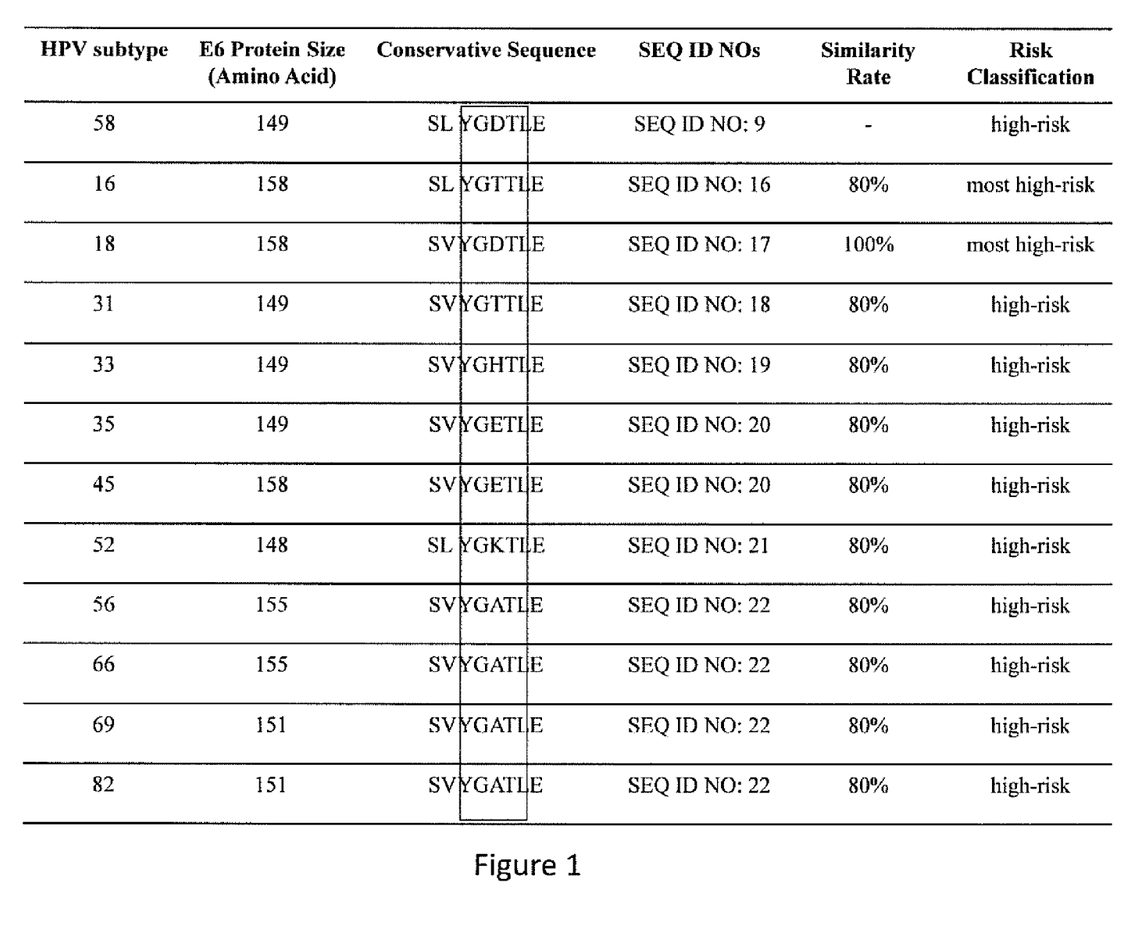
FIG. 1. Conservative analysis of the minimal motif of HPV58-E6 Protein E6-2 epitope with the homologous proteins of HR-HPVs. The YGDTL sequence of the HPV58/E6-2 epitope in the box is of 100% conservative with the corresponding sequence of HPV18-E6 protein, and is also highly conserved among the homologous proteins of other representative HR-HPVs, in which there is a residue difference at the same position, but these conserved sequences expressed by the 8-mer peptides fused with the truncated GST188 can all be recognized by the polyclonal antibodies against recombinant E6 protein of HPV58. The similarity rates are calculated according to the five amino acid residues in the box.
Figure 2:
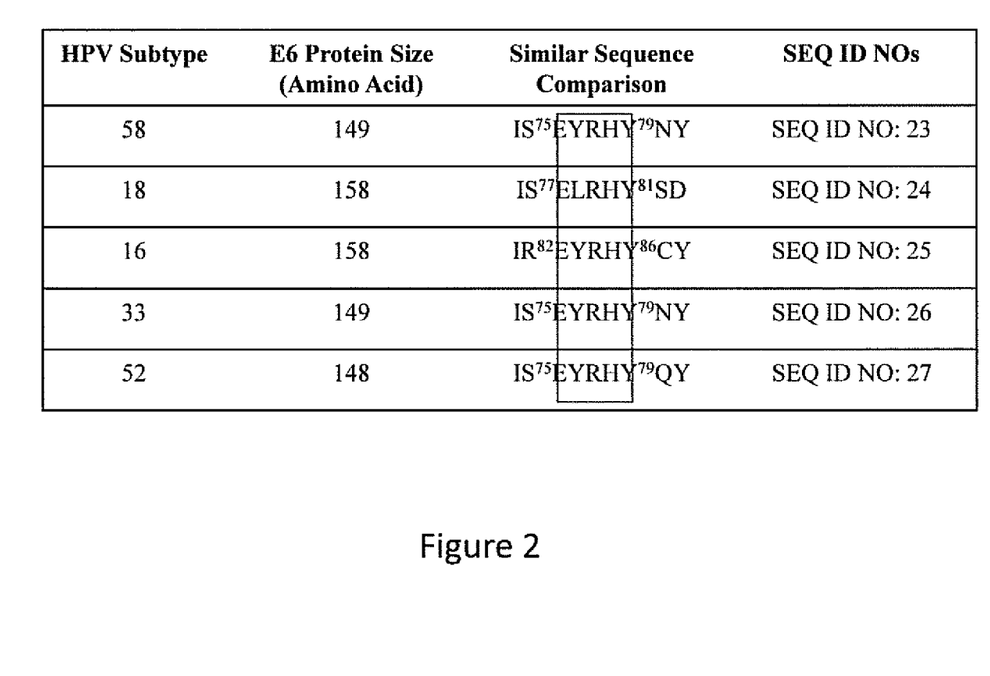
FIG. 2. Comparison of the sequences of the HPV homologous proteins that might be recognized as the epitope minimal motif by mAb C1P5 against HPV18-E6. The alignment of the similar sequences of the homologous proteins of high-risk HPVs is based on the in Western blotting that identified the reactive 9-mer peptide of the HPV58-E6 protein. The HPV18-E6 sequence in the box serves as the benchmark, and the five residues with only one residue difference might represent the possible range of epitope motifs that can be recognized by the mAb C1P5 against HPV18-E6.
Figure 3:
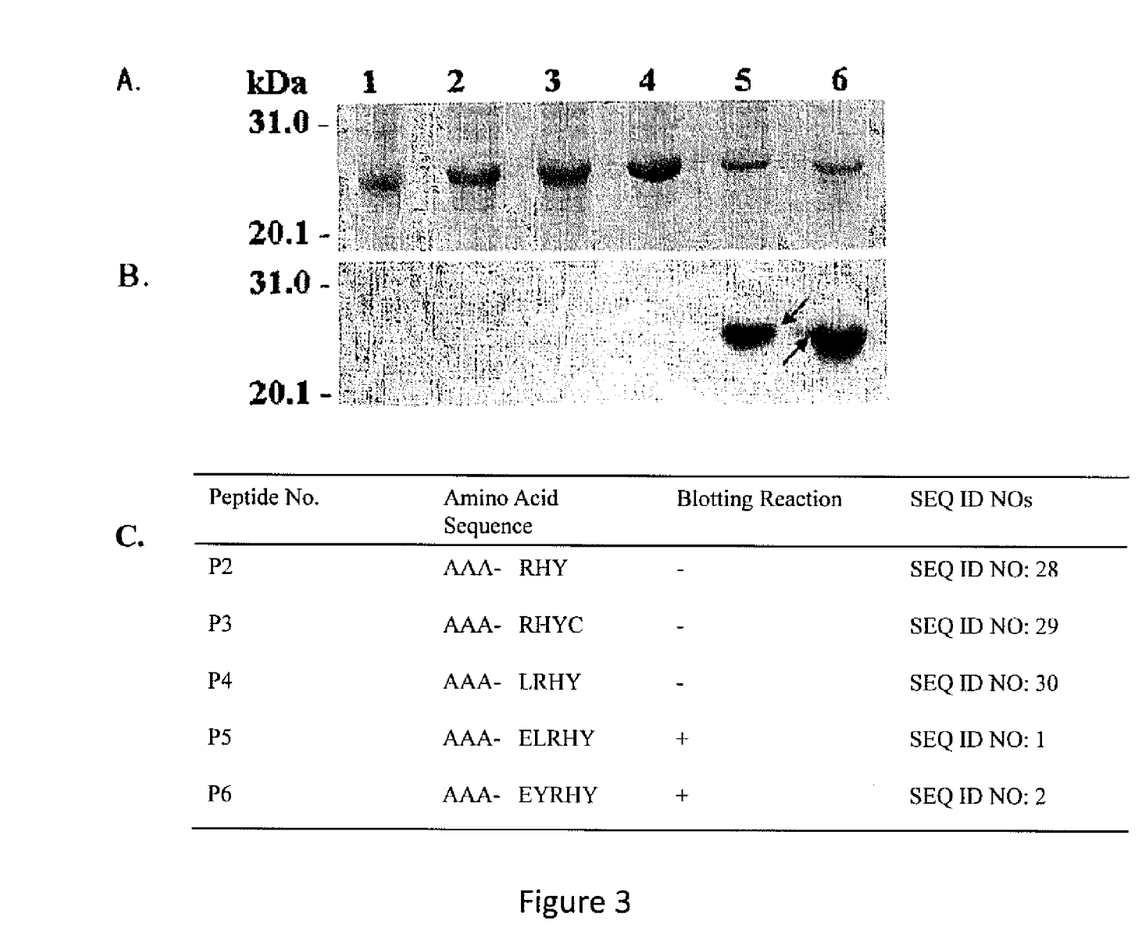
FIG. 3. SDS-PAGE analysis of the recombinant short peptides fused with truncated GST188 carrier proteins (A), Western blotting of the expressed short peptides using mAb C1P5 (B), and graphical list or analysis of the reactive epitope minimal motifs recognized by mAb C1P5 (C). (A): Lane 1: negative control GST188 protein; Lane 2~6: fusion proteins of GST188-P2~P6; (B): The arrows indicate reactive short peptides; (C): there are two intentions for adding three AAA residues in front of the short peptides: the first is to make it more convenient to synthesize the DNA fragment of the recombinant clones that are encoded by the short peptides; the second is to exclude the possible interference to epitope identifications that is caused by the two residues created at the restriction site of BamH I at the C-terminal of the GST188 carrier protein. The blotting results indicate that ELRHY pentapeptide is the binding minimal motif of mAb C1P5 and C1P5 also recognizes a conserved EYRHY sequence existed in the E6 proteins of HR-HPV16, 33, 52 and 58.

The inventors performed preliminary experiment, and the experimental results showed that the mAb C1P5 against HPV18-E6 protein also has cross-reactivity with HPV58-E6 protein in Western blotting, but do not recognize the octapeptide (SLYGDTLE: SEQ ID NO: 9) of HPV58/E6-2 epitope that is highly conservative among the homologous proteins of HR-HPVs (FIG. 1). Then, a series of overlapping 15-mer peptides (fused with GST188 carrier, P1-P23) with an overlap of 9 aa corresponding to the full-length sequence of HPV58-E6 protein were used to map antigenic 15-mer peptide using mAb C1P5 in Western blotting. The results showed that the mAb C1P5 could recognize two adjacent 15-mer peptides (LRLLSKISEYRHYNY; SEQ ID NO: 10 and ISEYRHYNYSLYGDT; SEQ ID NO: 11), suggesting that the mAb C1P5 recognizing-antigenic-site should be in the overlapping region of the nine residues (ISEYRHYNY: SEQ ID NO: 12). By comparing the amino acid sequences of the E6 proteins of HPV16, 18 and 58, the minimal motif recognized by mAb C1P5 was found to be further reduced to pentapeptide (EL/YRHY; SEQ ID NOs: 1 and 2) that has only one residue difference from each other (FIG. 2), because if the 6-mer peptides are formed by extending one residue at either left or right side, the sequences for HPV16and 18 have two residue differences, and cannot be recognized by mAb C1P5. Finally, in order to identify the epitope minimal motif recognized by mAb C1P5, four short-peptide (P2-P5) of HPV18-E6 and one short-peptide (P6) shared by HPV16-, 33-, 52- and 58-E6 were constructed and expressed (FIG. 3A). Of them only P5 and P6 were recognized by mAb C1P5 in Western blot test (FIG. 3B). Therefore, it is determined that the specific epitope minimal motif of HPV18-E6 recognized by mAb C1P5 is pentapeptide ELRHY, and that the pentapeptide (EYRHY: SEQ ID NO: 2) is conservative and generates the cross-reaction of mAb C1P5 with HPV16/HPV58E6proteins (FIG. 2, FIGS. 3B and 3C). Moreover, by comparing homologous protein sequences, it can be found that C1P5, a mAb against HPV18, can also have cross reactions with the E6 proteins of the high-risk HPV33 and HPV52 in addition to HPV16 and HPV58, since HPV33 and HPV52 also have the identical conservative sequence as the reactive pentapeptide of HPV16/HPV58 (FIG. 2).

Based on this new discovery, this invention provides a linear epitope minimal motif peptide, having the amino acid sequence as shown in EXRHY. In this sequence, X represents amino acid residue L or Y. The described peptides come from the E6 proteins of five HR-HPVs. As the format of choice, the described peptides have the sequences of amino acids as shown in SEQ ID NO: 1 (ELRHY) or SEQ ID NO: 2 (EYRHY).

Once the sequence of the described pentapeptide is identified, large amount of the peptide fused with a carrier protein can be produced by the genetic recombinant method. In this method, the DNA fragment encoding the peptide is usually cloned into a vector such as GST or truncated GST188, and then the cloned vector is transformed into a host cell. The short peptide fusion protein could be purified from the total proteins of the amplified host cells by the conventional method. In addition, in view of the short peptide nature of this invention, it might be better to employ chemical synthetic method (e.g., by peptide synthesizer) for preparing the mapped peptides in this invention. Such synthetic method is simple and rapid for preparing the peptides.

This invention meanwhile provides the identified epitope minimal motif peptide and its extended peptides for preparing "universal" preventive/therapeutic HPV vaccines comprising recombinant multiple-epitope peptides.

The epitope minimal motif peptide described in this invention can be used as an effective antigenic fragment of the E6 protein to induce an universal mAb or polyclonal antibodies (pAbs) targeting specifically at the E6 proteins of HR-HPV16, 18, 33, 52 and 58. The minimal motif peptide described in this invention can also be linked with other peptide or carrier protein acceptable in term of immunology (the selected carrier would be best to have no or weaker immunogenicity itself) to prepare antibodies as immunogen.

Antibodies can be prepared by various technologies that are known by the technical personnel in the field. For example, the purified recombinant peptide (or fused with other peptide segment or carrier protein acceptable in term of immunology) or chemical synthetic peptide can be used to immunize animals to induce the production of pAbs. The described antibodies can also be monoclonal antibodies (mAbs) which can be prepared by hybridoma technology (12-15). Polyclonal antibodies can be prepared by using the peptide of this invention to immunize animals, such as rabbits, mice, rats, and so on. Many kinds of adjuvants can be used to enhance the immune response, including but not limited to Freund's adjuvant.

This invention provides the application of the described epitope minimal motif peptides to detect the viruses of HPV16, HPV18, HPV33, HPV52 and HPV58 in the sample. With the information of the minimal motif peptides in this invention, the technical personnel in the field can sensitively detect the sequence or the encoding DNA sequence of the described epitope minimal motif peptides in the samples through a variety of techniques or methods, and such techniques or methods employed can be commonly used techniques in the biotechnical field, such as polymerase chain reaction (PCR).

This invention provides the application of the described epitope minimal motif peptides and their extended short peptides that can be alone (such as a chemical peptide or linked with GST188 carrier protein) or in combination (such as recombinant multiple epitope peptide) to prepare the detection antigens for serological diagnosis of the antibodies induced by the infection of HPV16, HPV18, HPV33, HPV52, and/or HPV58.

This invention also provides two highly conserved pentapeptides sequences of the mapped epitope, which can be used as biomarkers to determine HPV18 infection or other four HR-HPVs (HPV16, 33, 52 or 58) infections according to the translated aa sequences after PCR amplification of the HPV-E6 genes.

New Applications of mAb C1P5

In current existing technologies, it was found that the mAb C1P5 can only recognize HPV18-E6 protein and HPV16-E6 protein, but it was not clear whether the mAb C1P5 could recognize the E6 proteins of other HPV subtypes. This invention accidentally opened up the new applications of mAb C1P5, that is, it can bind to the E6 proteins of HR-HPV33, 52 or 58.

Therefore, this invention further provides the new applications of mAb C1P5 to prepare the test kits for detecting HR-HPV33, 52 and 58 infections, which are the new discoveries described in this invention.

This invention can be further described by the following examples. These examples do not mean to limit the scope of this invention as has been fully explained in the description above. For those experimental methods without specifying the conditions in the following examples, all are conducted according to the conventional or routine conditions and to the protocol of "Molecular Cloning: A Laboratory Manual" [the 3rd edition edited by Joe Sambrook and David Russell (USA) and translated by Peitang Huang (Science Press, China, 2002)] and the protocol of "Antibodies: A Laboratory Manual" [edited by Ed Harlow and David Lane (USA) and translated by Guanxin Shen (Science Press, China, 2002)] or the protocols recommended by the commercial manufacturers.

EXAMPLE

Fine Epitope Motif Mapping of HPV18-E6 Protein Using mAb C1P5

I. Materials:
1. The mouse mAb C1P5 against HPV18-E6 protein (16) was purchased from American Research Products (ARP) Inc. (commodity code: 12-6080A). In Western blotting experiments, the concentrations of mAb C1P5 were employed in reference to those recommended by the product manual or instructions.
2. The engineering bacteria encoding HPV58-E6 protein and the recombinant DNA clones of fusion proteins expressing a series of 15-mer peptides were provided by Shanghai Institute of Planned Parenthood Research, while the 15-mer peptides cover the whole sequence or domain of HPV58-E6 protein, overlapping each other by 9 amino acid residues (17). Refer to the invention patent for the construction of the fusion protein with the 8-mer peptides that contain the minimal motif YGDTL of E6-2 epitope (17).
3. The host bacteria E. coli BL21(DE3), the plasmid pXXGST-1 used for bio-synthesis of short peptides to precisely map the epitopes, and the plasmid pXXGST-2 to express truncated GST188 protein only used as negative control were all provided by Shanghai Institute of Planned Parenthood Research (18).
4. Restriction enzymes BamH I and Sal I as well as T4 DNA ligase were purchased from a Japanese company, TaKaRa Biotechnology. Ampicillin (Amp), pre-stained protein molecular weight standards, goat anti-rabbit-HRP (IgG/HRP) and 0.2 μm nitrocellulose membrane were purchased from Shanghai Sangon Biotech Services Company. The enhanced chemiluminescence (ECL) plus Western blotting detection reagents were purchased from GE Healthcare.
5. The plus and minus strands of DNA fragments were synthesized by Shanghai Jierui Biotech Co. Ltd, and these synthetic DNA fragments all have a BamH I cohesive end and a Sal I cohesive end at the 5' end and the 3' end respectively, which have a DNA sequence encoding a P2~P6 short peptide plus TAA termination codon between both ends (according to the genome sequence of HPV18, GenBank accession number: NC_001357).

6. The E6 protein sequences information for the following HR-HPVs is from GenBank database: for HPV16 (GenBank accession number: NC_001526), for HPV18 (GenBank accession number: NC_001357), for HPV33 (GenBank accession number: EU918766), for HPV52 (GenBank accession number: X74481), and for HPV58 (GenBank accession number: D90400).

II. Fine Epitope Mapping of HPV18-E6 Protein Using mAb C1P5:

1. The mAb C1P5-binding epitope motif is completely different from HPV58/E6-2 epitope (YGDTL; SEQ ID NO: 13).

As shown in FIG. 1, E6-2 epitope motif (YGDLE; SEQ ID NO: 14) on HPV58-E6 protein that was mapped by rabbit pAbs against recombinant HPV58-E6, exists at the end part of the HPV18-E6/2 antigenic peptide with 22 aa residues (IDFYSRIRELRHYSDSVYGDTL) (SEQ ID NO: 3) (as 100% identical). Also, there is only a residue difference (D.→T) between HPV58/E6-2epitope and the pentapeptide (YGTTL; SEQ ID NO: 15) (as 80% identical) present at the end part of E6/1 antigenic 10-mer peptide of HPV16-E6 that was mapped by rat pAbs (19), and the 8-mer peptides containing YGTTL (SEQ ID NO: 14) can also be recognized by rabbit pAbs against recombinant HPV58-E6 protein. Therefore, it was initially inferred that the mAb C1P5 might be able to recognize the HPV58/E6-2 epitope since mAb C1P5 can recognize both the HPV16-E6 and HPV18-E6 proteins (16). So the inventors made efforts to validate such an inference by employing mAb C1P5, and to investigate whether there is any change between the minimal motifs of both epitopes recognized by rabbit pAbs and mouse mAb. Thus, the inventors expressed HPV58-E6 protein and octapeptide fused with GST188 protein that contains HPV58/E6-2 motif (YGDTL: SEQ ID NO: 13), completed electrotransferring onto nitrocellulose membrane after SDS-PAGE, and finally carried out their immunoblotting using mAb C1P5.

HPV58-E6 protein and the fusion protein with an octapeptide containing HPV58/E6-2 motif (YGDTL: SEQ ID NO: 13) all have a sequence as SLYGDTLE (SEQ ID NO: 4).

The Immunoblotting results showed that mAb C1P5 could bind to HPV58-E6protein, but not to the short peptide containing E6-2 epitope motif (YGDTL; SEQ ID NO: 13).

2. Mapping the epitope recognized by mAb C1P5.

Since the mAb C1P5 can recognize the HPV58-E6 protein, further efforts is to identify its recognizing site. The inventors at first expressed a series of 15-mer peptides (fused with GST188 carrier protein), covering the whole sequence of HPV58-E6 protein (149 aa), overlapping each other by 9 amino acid residues (totally of 23 short peptides, No. P1~No. P23, of which the last one is a 17-mer peptide). Then each total cell proteins of the induced recombinant clones was transferred onto nitrocellulose membrane after running SDS-PAGE, and finally the immunoblotting test was carried out with mAb C1P5.

As a result, mAb C1P5 can recognize two adjacent 15-mer peptides of

```
                                    (SEQ ID NO: 5)
        P12-LRLLSKISEYRHYNY
        and
                                    (SEQ ID NO: 6)
        P13-ISEYRHYNYSLYGDT
``` with 9 overlapping amino acid residues. Therefore, the mAb-recognizing site can be determined to be in the region within the overlapping 9 residues (ISEYRHYNY) (SEQ ID NO: 7).

3. Sequence analysis for finding the minimal motif recognized by mAb C1P5.

In order to reduce the number in constructing and expressing short peptides for fine epitope mapping, sequence alignment of the HPV16-, 18- and 58-E6 proteins was performed on the basis of the 9 residues sequence identified above and according to the public information of these homologous proteins.

As shown in FIG. 2, the probable epitope minimal motif recognized by C1P5is reduced to the 5-mer peptide EYL/XRHY (SEQ ID NOs: 1 and 2: with only one residue difference between the HPV16 and 18 E6 proteins), since two residues difference would occur if extending one residue either at N terminal or C terminal.

4. Mapping the epitope minimal motif of pentapeptide EYRHY on HPV18-E6

Since usually the minimal motif recognized by monoclonal antibody has 1-2residues less than that recognized by polyclonal antibodies, four short peptides (adding 3 alanine residues at the N-terminals, designated as P2-P5, fused with GST188 carrier protein) are each designed by reducing one residue one after one starting from the N-terminals, using the sequence of ELRHY (SEQ ID NO: 1) of HPV18-E6 as the benchmark (FIG. 3C). In addition, a P5 short peptide corresponding to HPV16- and 58-E6 and a P6 short peptide AAA-EYRHY (SEQ ID NO: 8) are designed. The sense and antisense strands of DNA fragments encoding these short peptides described-above were designed respectively according to the public HPV genome information (for the sense strand: adding 5'-gatcc to the 5' end and taag-3' at the 3' end; for the antisense strand: adding 5'-tcgactta at the 5' end and g-3' to the 3' end). All the DNA fragments as designed above were chemically synthesized by outside service provider.

The complementary DNA fragments at the concentration level of 1 or 2 OD$_{260}$ (optical density at wavelength of 260 nm) value were dissolved to 20 μmol/μl stock solution with ddH$_2$O (according to the DNA fragment synthesis reports); 10 μL stock solution and 20 μL ddH$_2$O were mixed in a 1.5 mL eppendorf tube and then heated at 94° C. for 5 mins before cooling to room temperature. In 15 μl of the reaction mixture, 2 μL annealing fragments, 1 μL of 200 ng/μL pXXGST-1 plasmids (having sequence encoding GST188) digested with BamH I and Sal I, 1 μL T4 DNA ligase and 1.5 μL buffer were mixed and incubated overnight. The ligation solution was transformed into BL21(DE3) host, then the bacteria was smeared on the Luria Broth medium (LB) plates containing ampicillin. After overnight culture at 37□, the growing colonies (one colony for one clone) on the LB plate were inoculated into 3 mL LB medium for thermo-inducible expression. Each recombinant clone to express GST188-short peptide (P2-P6) fusion proteins was analyzed and verified through 15% SDS-PAGE. Each short peptide fusion protein has about 1 kDa mobility difference from the control GST188 protein expressed by pXXGST-2 plasmid. Each recombinant clone was picked and cultured for DNA sequencing.

Each recombinant clone confirmed by DNA sequencing was inoculated into 3 mL LB medium containing ampicillin and cultured overnight at 30° C. with shaking. The inoculums (or cultured solution) was inoculated into fresh LB medium containing ampicillin at 1:50 (inoculums: fresh medium) and cultured at 30° C. with shaking for 2~3 hrs until OD$_{600}$ reaches 0.6~0.8. After the temperature was up-regulated to 42° C., the culture solution was incubated for 4 hr for heat inducing expression. Then the bacteria were harvested by centrifugation, and were added with lysate, and finally were boiled for 5 min for further usage.

Each harvested cell total proteins was separated with 15% SDS-PAGE (two gels). After electrophoresis, one gel was stained with Coomassie blue, while the other gel was electrotransferred onto 0.2 μm nitrocellulose membrane at 100 mA for 2 hrs. The membrane was stained with ponceaux for 2 mins. The expressed bands of target short peptide fusion protein were marked by punching holes and then were washed off the ponceaux.

The membrane was washed with PBS buffer for four times and then blocked with 5% skimmed milk powder overnight. After additional washing with PBS buffer for four times, the membrane was incubated for 2 hrs at room temperature in 8.about.10 ml reaction solution mixed with 1 μL of mAb C1P5. After washing with PBS buffer, the membrane was incubated for 1 hr at room temperature in 10 ml of reaction solution mixed with 5 μL of goat anti rat IgG/HRP. Finally the membrane was washed with PBS buffer, and then the blot was developed by using enhanced chemiluminescence (ECL) plus Western blotting detection reagents. According to the results of the immunoblotting, it was confirmed that the P5 and P6 are the reactive short peptide (fusion protein), and that the epitope minimal motif recognized by mAb C1P5 is ELRHY (SEQ ID NO: 1) for HPV18-E6 protein, and that the mAb C1P5has cross-reactivity with the conservative pentapeptide EYRHY of the HPV16 and 58E6 homologous proteins.

5. Analysis of the cross-reactivity of mAb C1P5 with other HPV homologous proteins.

According to the public sequence information from the GenBank database on the homologous proteins of HR-HPVs, it was found that mAb C1P5 also has cross-reactivity with the E6 proteins of HR-HPV33 and 52 after performing sequence alignment of all HPV homologous E6 proteins, since they have the conservative peptide sequences of EL/YRHY (SEQ ID NOs: 1 and 2)as well (FIG. 2).

This invention describes the linear epitope minimal motif on E6 protein of HPV18 that can be recognized by mAb C1P5 (note: since a 22-mer peptides containing this minimal motif was published earlier, the extended 20-mer peptide of this invention no longer has novelty, and thus the extended 20-mer peptides are excluded for patent claims. But the novelty of the minimal motif as the enclosed epitope peptide is obvious. The same are as below). The minimal motif peptide can be used as the B-cell epitope candidate by itself or in combination with others to prepare "universal" preventive/therapeutic HPV vaccines comprising multiple epitopes. The minimal motif peptide can also be used as the B-cell epitope candidate by itself or in combination with others to prepare detection antigen comprising multiple epitopes for serological detection of the antibodies induced by the infection of the described high-risk HPVs. Such detection antigen can be prepared by employing either chemically synthetic or bio-engineering approach. In addition, this invention also provides a conserved pentapeptide sequence (EYRHY: SEQ ID NO: 2) with which the mAb C1P5 has cross reaction. The pentapeptide sequence can be used as reference peptide sequence alone or in combination with the highly conservative E6-2 epitope motif of HPV58 (YG -D/X-TL, where X represents D for HPV18 and 58, H for HPV33, K for HPV52, and T for HPV16) to diagnose the five HR-HPVs infection (HPV16, HPV18, HPV33, HPV52, and/or HPV58 as shown in FIG. 1) after PCR amplification of their HPV-E6 genes or its fragments. The highly conservative E6-2 epitope motif of HPV58 exists in the E6 proteins of almost all known and probable HR-HPVs.

The above specification includes numerous citations, publications and texts. Each is here incorporated by reference for all purposes as if fully set forth. The above specification, examples, and data provide a complete description of the preparation and use of the composition of the invention. It is obvious to the technical personnel in the relevant field of the research that the minimal motif of the epitope and its fusion protein described in this invention can be modified or changed without departing from the spirit and scope of the invention. Therefore, the appended claims cover all of these changes within the scope of the invention.

LITERATURE CITED 1. de Villiers E M, Fauquet C, Broker T R, et al. Classification of papillomaviruses. Virology 2004; 324: 17-27.
2. Parkin D M. The global health burden of infection-associated cancers in the year 2002. Int J Cancer 2006; 118: 3030-3044.
3. de Sanjose S, Quint W G, Alemany L, et al. Human papillomavirus genotype attribution in invasive cervical cancer: a retrospective cross-sectional worldwide study. Lancet Oncol 2010; 11(11): 1048-1056.
4. Wheeler C M, Castellsague X, Garland S M, et al. Cross-protective efficacy of HPV16/18 ASO4-adjuvanted vaccine against cervical infection and precancer caused by non-vaccine oncogenic HPV types: 4-year end-of-study analysis of the randomized, double-blind PATRICIA trial. Lancet Oncol 2012; 13(1): 100-110.
5. Huang S, Afonina I, Miller B A, Beckmann A M. Human papillomavirus type 52 and 58 are prevalent in cervical cancers from Chinese woman. Int J Cancer 1997; 70(4): 408-411.
6. Dillner J. Mapping of linear epitopes of human papillomavirus type 16: the E1, E2, E4, E5, E6 and E7 open reading frames. Int J Cancer 1990; 46:703-711.
7. Dillner J, Dillner L, Cheng H M. Synthetic peptides in human papillomavirus 1, 5, 6, 8, 11, 16, 18, 31, 33 and 56, useful in immunoassay for diagnostic purposes. U.S. Pat. No. 5,932,412, 1999.
8. Xu W X, et al. Minimal motifs of epitopes of human papillomavirus type 58E6 protein; China patent no.: 200910196693.5.
9. Bleul C, Muller M, Frank R, et al. Human papillomavirus type 18 E6 and E7 antibodies in human sera: increased anti-E7 prevalence in cervical cancer patients. J Clin Microbiol 1991; 29(8): 1579-1588.
10. Banks L, Spence P, Androphy E, et al. Identification of human papillomavirus type 18 E6 polypeptide in cells derived from human cervical carcinomas. J Gen Virol 1987; 68 (Pt 5): 1351-1359.
11. Bleul C, Muller M, Frank R, et al. human Papillomavirus type 18 E6 and E7 antibodies in human sera: increased anti-E7 prevalence in cervical cancer patients. J Clin Microbiol 1991; 29(8): 1579-1588.
12. Kohler G, et al. Continue culture of fused cell secreting antibody of predefined specificity. Nature 1975; 256: 495-497.
13. Kohler G, et al. Derivation of specific antibody-producing tissue culture and tumor lines by cell fusion. Eur J Immunol 1976; 6: 511-519.
14. Kohler G, et al. Fusion between immunoglobulin-secreting and non-secreting myeloma cell lines. Eur J Immunol 1976; 6: 292-295.
15. Hammerling G J, et al, In monoclonal antibodies and T cell hybridomas, Elsevier, N. Y., 1981.

16. Banks L, Spence P, Androphy E, et al. The identification of human papillomavirus type 18 E6 polypeptide in cells derived from human cervical carcinomas. J Gen Virol 1987; 68 (Pt): 1351-1359.
17. Xu W et al, Minimal motifs of linear B-cell epitopes in E6 protein from human papillomavirus type 58. China Patent No.: ZL 2009 1 0196693.5.
18. Xu W X, et al. Minimal motif mapping of a known epitope on human zona pellucida protein-4 using a peptide biosynthesis strategy. J Reprod Immunol 2009; 81: 9-16.
19. Gao L, et al. Immune response to human papillomavirus type 16 E6 gene in a live vaccinia vector. J Gen Virol 1994; 75: 157-164.

The invention claimed is:

1. A method for preparing immunogens or antigens for E6 proteins of HPV18, HPV16, HPV52, HPV53, or HPV58, comprising:
constructing a synthetic peptide comprising a minimal motif of B-cell epitope present in an E6 protein of a human papillomavirus (HPV), wherein the minimal motif of B-cell epitope is a peptide of 5 amino acid residues in length consisting of EXRHY; wherein X represents the amino acid L or Y; and wherein the minimal motif of B-cell epitope is directly fused with a peptide sequence that is not from a HPV protein.

2. The method of claim 1, wherein the synthetic peptide further comprises one or more additional copy of the minimal motifs of B-cell epitope.

3. The method of claim 1, wherein the synthetic peptide further comprises an additional HPV immunogenic or antigenic sequence.

4. A method for preparing an antibody that can bind specifically with an E6 protein of HPV18, HPV16, HPV52, HPV33, or HPV58, comprising immunizing with the synthetic peptide prepared according to claim 1.

5. A method for preparing a detection antigen for serological diagnosis of HPV infection, comprising coupling the synthetic peptide prepared according to claim 1 with another epitope to form a detection antigen with multiple epitopes.

* * * * *

UNITED STATES PATENT AND TRADEMARK OFFICE
CERTIFICATE OF CORRECTION

PATENT NO. : 9,884,894 B2
APPLICATION NO. : 14/907421
DATED : February 6, 2018
INVENTOR(S) : Riting Liu et al.

Page 1 of 1

It is certified that error appears in the above-identified patent and that said Letters Patent is hereby corrected as shown below:

On the Title Page

Under item (71), Applicants: "Guangzhou Hengsun Pharmaceutical Technology Co. Ltd., Guangzhou (CN);" should be -- Guangdong Nanwan Pharmaceutical Technology Co. Ltd., Guangzhou (CN); --.

Signed and Sealed this
Fourth Day of June, 2019

Andrei Iancu
*Director of the United States Patent and Trademark Office*